(12) United States Patent
Ye

(10) Patent No.: US 11,987,589 B2
(45) Date of Patent: May 21, 2024

(54) HETEROCYCLIC FLAVONE DERIVATIVES, COMPOSITIONS, AND METHODS RELATED THERETO

(71) Applicant: Emory University, Atlanta, GA (US)

(72) Inventor: Keqiang Ye, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 656 days.

(21) Appl. No.: 17/266,863

(22) PCT Filed: Aug. 7, 2019

(86) PCT No.: PCT/US2019/045585
§ 371 (c)(1),
(2) Date: Feb. 8, 2021

(87) PCT Pub. No.: WO2020/033604
PCT Pub. Date: Feb. 13, 2020

(65) Prior Publication Data
US 2021/0292335 A1  Sep. 23, 2021

Related U.S. Application Data

(60) Provisional application No. 62/715,764, filed on Aug. 7, 2018.

(51) Int. Cl.
*A61K 9/00* (2006.01)
*A61K 31/4184* (2006.01)
(Continued)

(52) U.S. Cl.
CPC ........ *C07D 491/052* (2013.01); *A61K 9/0053* (2013.01); *A61K 31/4184* (2013.01); *A61P 25/24* (2018.01); *A61P 25/28* (2018.01)

(58) Field of Classification Search
CPC .............. C07D 491/052; A61K 9/0053; A61K 31/4184; A61P 25/28; A61P 25/24
See application file for complete search history.

(56) References Cited

U.S. PATENT DOCUMENTS

| 6,369,086 B1 | 4/2002 | Davis et al. |
| 6,369,087 B1 | 4/2002 | Whittle et al. |

(Continued)

FOREIGN PATENT DOCUMENTS

| WO | 2010011836 | 1/2010 |
| WO | 2010107866 | 9/2010 |

(Continued)

OTHER PUBLICATIONS

Ravishankar, D. et al. Thioflavones as novel neuroprotective agents Bioorganic and Medicinal Chemistry 24 (2016) 5513-5520. (Year: 2016).*

(Continued)

*Primary Examiner* — Mark L Shibuya
*Assistant Examiner* — Kevin S Martin
(74) *Attorney, Agent, or Firm* — Kilpatrick Townsend & Stockton LLP

(57) ABSTRACT

In certain embodiments, the disclosure relates to heterocyclic flavone derivatives, such as those described by formula provided herein, pharmaceutical compositions, and methods related thereto. In certain embodiments, the disclosure relates to methods of treating or preventing diseases or conditions related to BDNF and TrkB activity, such as depression, stroke, Rett syndrome, Parkinson's disease, and Alzheimer's disease by administering effective amounts of pharmaceutical compositions comprising compounds disclosed herein to a subject in need thereof.

14 Claims, 6 Drawing Sheets

(51) Int. Cl.
A61P 25/24 (2006.01)
A61P 25/28 (2006.01)
C07D 491/052 (2006.01)

(56) References Cited

U.S. PATENT DOCUMENTS

| | | | |
|---|---|---|---|
| 6,372,733 | B1 | 4/2002 | Caldwell et al. |
| 6,372,778 | B1 | 4/2002 | Tung et al. |
| 7,576,128 | B2 | 8/2009 | Hu et al. |
| 8,299,092 | B2 | 10/2012 | Krejci et al. |
| 8,563,596 | B2 | 10/2013 | Sivakumar et al. |
| 2007/0254933 | A1 | 11/2007 | Jung et al. |
| 2016/0022642 | A1 | 1/2016 | Crews et al. |

FOREIGN PATENT DOCUMENTS

| | | | |
|---|---|---|---|
| WO | 2011156479 | 12/2011 | |
| WO | 2014018741 | 1/2014 | |
| WO | WO-2014018741 A1 * | 1/2014 | ........... A61K 31/352 |

OTHER PUBLICATIONS

Hoffmann-Roder, A., Diederich, F. Nucleophilic perfluoroalkylation of cyclic imides with (perfluoroalkyl)trimethylsilanes Abstracts of Papers, 228th ACS National Meeting, Philadelphia, PA, United States, Aug. 22-26, 2004 (Year: 2004).*
EP19847006.4 , "Intention to Grant", dated Apr. 17, 2023, 8 pages.
PCT/US2019/045585 , "International Preliminary Report on Patentability", dated Feb. 18, 2021, 5 pages.
European Application No. 19847006.4, Extended European Search Report dated Mar. 14, 2022, 7 pages.
International Application No. PCT/US2019/045585, International Search Report and the Written Opinion dated Nov. 5, 2019, 6 pages.
Adamczuk et al., Polymorphism of Brain Derived Neurotrophic Factor Influences β Amyloid Load in Cognitively Intact Apolipoprotein E ε4 Carriers, Neuroimage Clinical, vol. 2, No. 1, Apr. 2013, pp. 512-520.
Andero et al., Effect of 7,8-Dihydroxyflavone, a Small-Molecule TrkB Agonist, on Emotional Learning, American Journal of Psychiatry, vol. 168, No. 2, Feb. 2011, pp. 163-172.
Ando et al., Animal Model of Dementia Induced by Entorhinal Synaptic Damage and Partial Restoration of Cognitive Deficits by BDNF and Carnitine, Journal of Neuroscience Research, vol. 70, No. 3, Nov. 1, 2002, pp. 519-527.
Arancibia et al., Protective Effect of BDNF Against Beta-Amyloid Induced Neurotoxicity in Vitro and in Vivo in Rats, Neurobiology of Disease, vol. 31, No. 3, Sep. 2008, pp. 316-326.
Arancio et al., Neurotrophins, Synaptic Plasticity and Dementia, Current Opinion in Neurobiology, vol. 17, No. 3, Jul. 2007, pp. 325-330.
Atasoy et al., Both Secreted and the Cellular Levels of BDNF Attenuated Due to Tau Hyperphosphorylation in Primary Cultures of Cortical Neurons, Journal of Chemical Neuroanatomy, vol. 80, Mar. 2017, pp. 19-26.
Aytan et al., Protective Effects of 7,8-Dihydroxyflavone on Neuropathological and Neurochemical Changes in a Mouse Model of Alzheimer's Disease, European Journal of Pharmacology, vol. 828, Jun. 5, 2018, 21 pages.
Castello et al., 7,8-Dihydroxyflavone, a Small Molecule TrkB Agonist, Improves Spatial Memory and Increases Thin Spine Density in a Mouse Model of Alzheimer Disease-Like Neuronal Loss, PLoS One, vol. 9, No. 3, Mar. 10, 2014, pp. 1-8.
Castello et al., Genetic Knockdown of Brain-Derived Neurotrophic Factor in 3xTg-AD Mice Does Not Alter aβ or Tau Pathology, PLoS One, vol. 7, No. 8, Aug. 2012, pp. 1-6.
Chen et al., Optimized TrkB Agonist Ameliorates Alzheimer's Disease Pathologies and Improves Cognitive Functions via Inhibiting Delta-Secretase, ACS Chemical Neuroscience, vol. 12, Jun. 9, 2021, pp. 2448-2461.
Chen et al., Tau Protein is Involved in Morphological Plasticity in Hippocampal Neurons in Response to BDNF, Neurochemistry International, vol. 60, No. 3, Feb. 2012, pp. 233-242.
Chen et al., The Prodrug of 7,8-Dihydroxyflavone Development and Therapeutic Efficacy for Treating Alzheimer's Disease, Proceedings of the National Academy of Sciences of the United States of America, vol. 115, No. 3, Jan. 16, 2018, pp. 578-583.
Chiruta et al., Chemical Modification of the Multitarget Neuroprotective Compound Fisetin, Journal of Medicinal Chemistry, vol. 55, No. 1, Jan. 12, 2012, pp. 378-389.
Choi et al., Prelimbic Cortical BDNF is Required for Memory of Learned Fear but not Extinction or Innate Fear, Proceedings of the National Academy of Sciences of the United States of America, vol. 107, No. 6, Feb. 9, 2010, pp. 2675-2680.
Devi et al., 7,8-Dihydroxyflavone, a Small-Molecule TrkB Agonist, Reverses Memory Deficits and BACE1 Elevation in a Mouse Model of Alzheimer's Disease, Neuropsychopharmacology, vol. 37, No. 2, Jan. 2012, pp. 434-444.
Devi et al., TrkB Reduction Exacerbates Alzheimer's Disease-Like Signaling Aberrations and Memory Deficits without Affecting β-Amyloidosis in 5XFAD Mice, Translational Psychiatry, vol. 5, No. 5, May 5, 2015, pp. 1-9.
Dwivedi, Brain-Derived Neurotrophic Factor: Role in Depression and Suicide, Neutopsychiatric Disease and Treatment, vol. 5, Aug. 2009, pp. 433-449.
Elliott et al., Brain-Derived Neurotrophic Factor Induces a Rapid Dephosphorylation of Tau Protein Through a PI-3 Kinase Signalling Mechanism, European Journal of Neuroscience, vol. 22, No. 5, Sep. 2005, pp. 1081-1089.
Gao et al., TrkB Activation by 7, 8-Dihydroxyflavone Increases Synapse AMPA Subunits and Ameliorates Spatial Memory Deficits in a Mouse Model of Alzheimer's Disease, Journal of Neurochemistry, vol. 136, No. 3, Feb. 2016, pp. 620-636.
Hongpaisan et al., PKC ε Activation Prevents Synaptic Loss, aβ Elevation, and Cognitive Deficits in Alzheimer's Disease Transgenic Mice, The Journal of Neuroscience Research, vol. 31, No. 2, Jan. 12, 2011, pp. 630-643.
Huang et al., Trk Receptors: Roles in Neuronal Signal Transduction, Annual Review of Biochemistry, vol. 72, No. 1, Feb. 2003, pp. 609-642.
Jang et al., A Selective TrkB Agonist with Potent Neurotrophic Activities by 7,8-Dihydroxyflavone, Proceedings of the National Academy of Sciences of the United States of America, vol. 107, No. 6, Feb. 9, 2010, pp. 2687-2692.
Kaplan et al., A DRD4/BNDF Gene-Gene Interaction Associated with Maximum BMI in Women with Bulimia Nervosa, International Journal of Eating Disorders, vol. 41, No. 1, Jan. 2008, pp. 22-28.
Leuzy et al., Longitudinal Tau and Metabolic PET Imaging in Relation to Novel CSF Tau Measures in Alzheimer's Disease, European Journal of Nuclear Medicine and Molecular Imaging, vol. 46, No. 5, May 2019, 12 pages.
Lim et al., BDNF Val66Met, Aβ Amyloid, and Cognitive Decline in Preclinical Alzheimer's Disease, Neurobiology of Aging, vol. 34, No. 11, Nov. 2013, pp. 2457-2464.
Liu et al., A Synthetic 7,8-Dihydroxyflavone Derivative Promotes Neurogenesis and Exhibits Potent Antidepressant Effect, Journal of Medicinal Chemistry, vol. 53, No. 23, Dec. 9, 2010, pp. 8274-8286.
Liu et al., Biochemical and Biophysical Investigation of the Brain-Derived Neurotrophic Factor Mimetic 7,8-Dihydroxyflavone in the Binding and Activation of the TrkB Receptor, Journal of Biological Chemistry, vol. 289, No. 40, Oct. 3, 2014, pp. 27571-27584.
Liu et al., Optimization of a Small Tropomyosin-Related Kinase B (Trkb) Agonist 7,8-Dihydroxyflavone Active in Mouse Models of Depression, Journal of Medicinal Chemistry, vol. 55, No. 19, Oct. 11, 2012, pp. 8524-8537.
Maina et al., Serum Levels of Brain-Derived Neurotrophic Factor in Drug-Narve Obsessive-Compulsive Patients: A Casecontrol Study, Journal of Affective Disorders, vol. 122, Nos. 1-2, Apr. 2010, pp. 174-178.
Matrone et al., NGF and BDNF Signaling Control Amyloidogenic Route and Abeta Production in Hippocampal Neurons, Proceedings of the National Academy of Sciences, vol. 105, No. 35, Sep. 2, 2008, pp. 13139-13144.

(56) References Cited

OTHER PUBLICATIONS

Mattson, Pathways Towards and Away from Alzheimer's Disease, Nature, vol. 430, No. 7000, Aug. 5, 2004, pp. 631-639.
Mercader et al., Blood Levels of Brain-Derived Neurotrophic Factor Correlate with Several Psychopathological Symptoms in Anorexia Nervosa Patients, Neuropsychobiology, vol. 56, No. 4, 2007, 13 pages.
Michalski et al., Brain-Derived Neurotrophic Factor and TrkB Expression in the "Oldest-Old, the 90+ Study: Correlation with Cognitive Status and Levels of Soluble Amyloid-Beta", Neurobiology of Aging, vol. 36, No. 12, Dec. 2015, pp. 3130-3139.
Murer et al., An Immunohistochemical Study of the Distribution of Brain-Derived Neurotrophic Factor in the Adult Human Brain, with Particular Reference to Alzheimer's Disease, Neuroscience, vol. 88, No. 4, Feb. 1999, pp. 1015-1032.
Murer et al., Brain-Derived Neurotrophic Factor in the Control Human Brain, and in Alzheimer's Disease and Parkinson's Disease, Progress in Neurobiology, vol. 63, No. 1, Jan. 2001, pp. 71-124.
Nagahara et al., Neuroprotective Effects of Brain-Derived Neurotrophic Factor in Rodent and Primate Models of Alzheimer's Disease, Nature Medicine, vol. 15, No. 3, Mar. 2009, pp. 331-337.
Obianyo et al., Novel Small Molecule Activators of the Trk Family of Receptor Tyrosine Kinases, Biochimica et Biophysica Acta, vol. 1834, No. 10, Oct. 2013, pp. 2213-2218.
Ochs et al., A Phase I/II Trial of Recombinant Methionyl Human Brain Derived Neurotrophic Factor Administered by Intrathecal Infusion to Patients with Amyotrophic Lateral Sclerosis, Amyotrophic Lateral Sclerosis and Other Motor Neuron Disorders, vol. 1, No. 3, Jun. 2000, pp. 201-206.
Peng et al., Decreased Brain-Derived Neurotrophic Factor Depends on Amyloid Aggregation State in Transgenic Mouse Models of Alzheimer's Disease, Journal of Neuroscience, vol. 29, No. 29, Jul. 22, 2009, pp. 9321-9329.
Rohe et al., Brain-Derived Neurotrophic Factor Reduces Amyloidogenic Processing through Control of SORLA Gene Expression, The Journal of Neuroscience, vol. 29, No. 49, Dec. 9, 2009, pp. 15472-15478.
Shankar et al., Alzheimer's Disease: Synaptic Dysfunction and Abeta, Molecular Neurodegeneration, vol. 4, No. 48, Nov. 23, 2009, pp. 1-13.
Sousa et al., Flavone-Nitrogen Heterocycle Conjugate Fomnation by 1,3-Dipolar Cycloadditions, European Journal of Organic Chemistry, vol. 1, Jan. 2012, pp. 132-143.
Vassar et al., The Beta-Secretase Enzyme BACE in health and Alzheimer's Disease: Regulation, Cell Biology, Function, and Therapeutic Potential, Journal of Neuroscience, vol. 29, No. 41, Oct. 14, 2009, pp. 12787-12794.
Wang et al., BDNF Inhibits Neurodegenerative Disease-Associated Asparaginyl Endopeptidase Activity via Phosphorylation by AKT, JCI Insight, vol. 3, No. 16, Aug. 23, 2018, pp. 1-21.
Wang et al., C/EBPβ Regulates Delta-Secretase Expression and Mediates Pathogenesis in Mouse Models of Alzheimer's Disease, Nature Communications, vol. 9, No. 1, May 2018, pp. 1-16.
Windisch et al., Specific Neurotrophin Binding to Leucine-Rich Motif Peptides of TrkA and TrkB, FEBS Letters, vol. 374, No. 1, Oct. 23, 1995, pp. 125-129.
Xiu et al., Decreased Serum BDNF Levels in Chronic Institutionalized Schizophrenia on Long-term Treatment with Typical and Atypical Antipsychotics, Progress in Neuro-Psychophamnacology and Biological Psychiatry, vol. 33, No. 8, Nov. 13, 2009, pp. 1508-1512.
Yushchenko et al., Synthesis and Fluorescence Properties of 2-aryl-3-hydroxyquinolones, A New Class of Dyes Displaying Dual Fluorescence, Tetrahedron Letters, vol. 47, No. 6, Feb. 6, 2006, pp. 905-908.
Zajac et al., Wheel Running and Environmental Enrichment Differentially Modify Exon-specific BDNF Expression in the Hippocampus of Wild-type and Pre-motor Symptomatic Male and Female Huntington's Disease Mice, Hippocampus, vol. 20, No. 5, May 2010, pp. 621-636.
Zeev et al., The Common BDNF Polymorphism may be a Modifier of Disease Severity in Rett Syndrome, Neurology, vol. 72, No. 14, Apr. 7, 2009, pp. 1242-1247.
Zhang et al., 7,8-Dihydroxyflavone Prevents Synaptic Loss and Memory Deficits in a Mouse Model of Alzheimer's Disease, Neuropsychopharmacology, vol. 39, No. 3, Feb. 2014, pp. 638-650.
Zhang et al., Asparagine Endopeptidase Cleaves α-synuclein and Mediates Pathologic Activities in Parkinson's Disease, Nature Structural & Molecular Biology, vol. 24, No. 8, Aug. 2017, pp. 632-642.
Zhang et al., Cleavage of Tau by Asparagine Endopeptidase Mediates the Neurofibrillary Pathology in Alzheimer's Disease, Nature Medicine, vol. 20, No. 11, Nov. 2014, pp. 1254-1262.
Zhang et al., Delta-Secretase Cleaves Amyloid Precursor Protein and Regulates the Pathogenesis in Alzheimer's Disease, Nature Communications, vol. 6, Nov. 9, 2015, pp. 1-16.
Zhang et al., Inhibition of Delta-Secretase Improves Cognitive Functions in Mouse Models of Alzheimer's Disease, Nature Communications, vol. 8, Mar. 27, 2017, pp. 1-17.
Zuccato et al., Brain-Derived Neurotrophic Factor in Neurodegenerative Diseases, Nature Reviews Neurology, vol. 5, No. 6, Jun. 1, 2009, pp. 311-322.

* cited by examiner

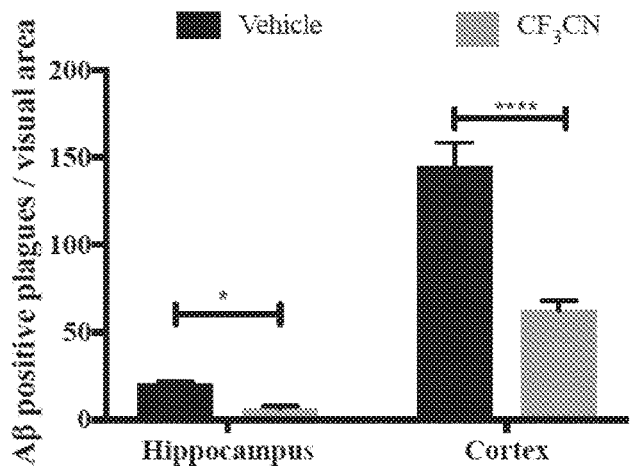
FIG. 3B
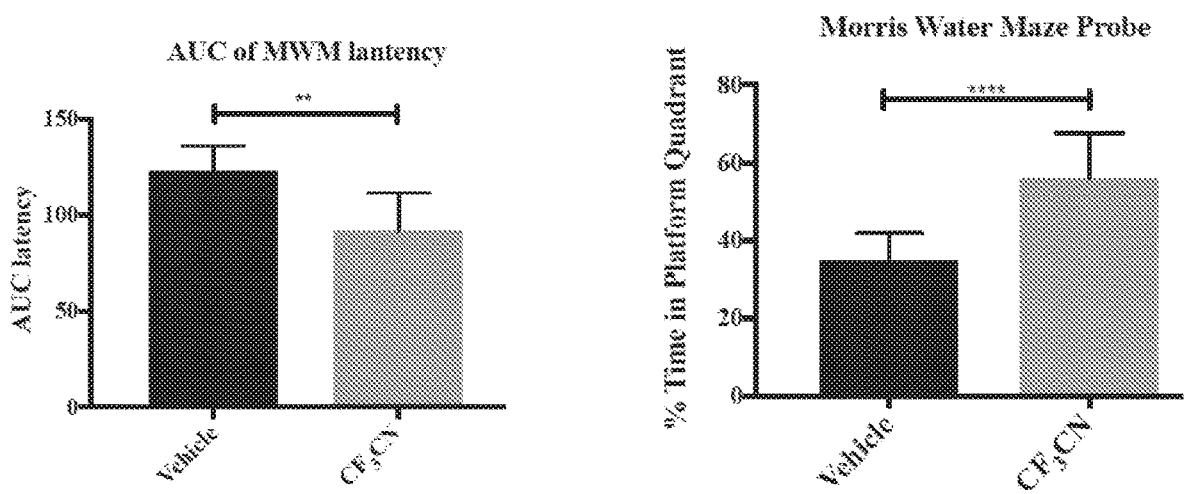
FIG. 3C
FIG. 3D

HETEROCYCLIC FLAVONE DERIVATIVES, COMPOSITIONS, AND METHODS RELATED THERETO

CROSS-REFERENCE TO RELATED APPLICATIONS

This application is the National Stage of International Application No. PCT/US2019/045585 filed Aug. 7, 2019, which claims the benefit of U.S. Provisional Application No. 62/715,764 filed Aug. 7, 2018. The entirety of each of these applications is hereby incorporated by reference for all purposes.

STATEMENT REGARDING FEDERALLY SPONSORED RESEARCH OR DEVELOPMENT

This invention was made with government support under CA186918 awarded by the National Institutes of Health. The government has certain rights in the invention.

BACKGROUND

Neurotrophins are growth factors regulate the development and maintenance of the peripheral and the central nervous system. Brain-derived neurotrophic factor (BDNF) is a member of the neurotrophin family, which includes nerve growth factor (NGF), NT-3 and NT-4/5. BDNF binding to its cognate receptor, TrkB, triggers its dimerization through conformational changes and autophosphorylation of tyrosine residues, resulting in activation of the three major signaling pathways—mitogen-activated protein (MAPK), phosphatidylinositol 3-kinase (PI3K) and phospholipase C-γ1 (PLC-γ1). Various studies have shown links between BDNF and TrkB to conditions such as depression, schizophrenia, obsessive-compulsive disorder, Alzheimer's disease, Huntington's disease, Rett syndrome, and dementia, as well as anorexia nervosa and bulimia nervosa. See Dwivedi, Neuropsychiatric Disease and Treatment, 2009, 5: 433-49; Xiu et al., Progress in Neuro-Psychopharmacology and Biological Psychiatry, 2009, 33(8):1508-12; Maina et al., Journal of Affective Disorders, 2010, 122(1-2):174-8; Zuccato et al., Nature Reviews Neurology, 2009, 5(6):311-22; Zajac et al., 2010, Hippocampus 20 (5): 621-36; Zeev et al., Neurology, 2009, 72 (14): 1242-7; Arancio et al., 2007, Current Opinion in Neurobiology, 17 (3): 325-30; Mercader et al, Neuropsychobiology, 2007, 56 (4): 185-90; Kaplan et al., International Journal of Eating Disorders, 2008 41 (1): 22-8.

It has been reported that certain 7,8-dihydroxyflavone derivatives promote neurogenesis and exhibits potent antidepressant effects. See Liu et al., J Med Chem, 2010, 53 (23), pp 8274-8286. See also WO/2014/018741, WO/2010/011836, WO/2010/107866, and WO 2011/156479. As 7,8-dihydroxyflavone derivatives are catechol and phenyl containing compounds, they are prone to be cleared in the circulatory system following oxidation, glucuronidation, sulfation, or methylation. Thus, there is a need to identify improved flavone derivatives with improved pharmacokinetic properties.

The health benefits of flavonoid compounds have been reported in a number of references, including neuroprotective and anti-cancer properties. See Chiruta et al., 2012, Journal of Medicinal Chemistry, 55, 378-89; Sousa et al., 2012, European Journal of Organic Chemistry, 1, 132-43; Sivakumar et al., U.S. Publication No. 2010/0179210. Derivatives of 3-hydroxyquinolone compounds have also been previously synthesized with reports of their fluorescence and biological activities disclosed. See Yushchenko et al., 2006, Tetrahedron Letters, 47, 905-8; Krejci et al., U.S. Publication No. 2010/0022587.

The references cited hereby are not an admission of prior art.

SUMMARY

In certain embodiments, the disclosure relates to substituted heterocyclic flavone derivatives, such as those described by formula provided herein, pharmaceutical compositions, and methods related thereto. In certain embodiments, the disclosure relates to methods of treating or preventing diseases or conditions related to BDNF and TrkB activity, such as depression, stroke, Rett syndrome, Parkinson's disease, and Alzheimer's disease by administering effective amounts of pharmaceutical compositions comprising compounds disclosed herein.

In certain embodiments, the disclosure related to a compound comprising Formula I.

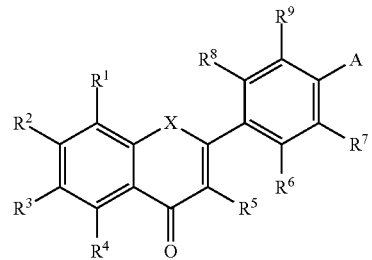

Formula I or salt, prodrug, or ester thereof wherein

X is O, S, or NH;

A is cyano (—CN);

$R^1$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^1$ is optionally substituted with one or more, the same or different, $R^{15}$; or $R^1$ and $R^2$ and attached atoms form a 5 membered heterocyclic ring, such as imidazolyl, optionally substituted with $R^{15}$;

$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;

$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;

$R^{15}$ is independently selected alkyl, halogen, nitro, cyano, hydroxy, amino, mercapto, formyl, alkanoyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and R[16] is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to pharmaceutical compositions comprising compounds disclosed herein and a pharmaceutically acceptable excipient. In certain embodiments, the pharmaceutical composition is in the form of a tablet, capsule, pill, or solution for injection. In certain embodiments, the pharmaceutical composition is in sterilized and pH buffered aqueous solution optionally comprising a saccharide or polysaccharide.

In certain embodiments, the disclosure relates to methods of preventing or treating a BDNF and TrkB related disease or condition comprising the administering an effective amount of a pharmaceutical composition disclosed herein, to a subject in need thereof. In some embodiments, the subject is diagnosed with, exhibiting symptoms of, or at risk of the disease or condition. In some embodiments, the disease or condition is depression, schizophrenia, obsessive-compulsive disorder, anorexia nervosa, bulimia nervosa, anxiety, amyotrophic later sclerosis, Alzheimer's disease, Huntington's disease, Rett syndrome, epilepsy, Parkinson's disease, dementia, diabetic neuropathy, peripheral neuropathy, obesity, peripheral nerve injury, pain, or stroke. In certain embodiments, the methods described herein include a method of improving memory, e.g., in a subject diagnosed with a dementia or related TrkB related disease or condition.

In certain embodiments, the disease is depression and the pharmaceutical composition is administered in combination with an anti-depressant such as a selective serotonin reuptake inhibitor such as citalopram, escitalopram, fluoxetine, fluvoxamine, paroxetine, sertraline, or vilazodone, a serotonin-norepinephrine reuptake inhibitor such as desvenlafaxine, duloxetine, milnacipran, venlafaxine, a noradrenergic and specific serotonergic antidepressant such as mianserin and mirtazapine, a norepinephrine reuptake inhibitor such as atomoxetine, mazindol, reboxetine, viloxazine, a norepinephrine-dopamine reuptake inhibitor such as bupropion, a selective serotonin reuptake enhancer such as tianeptine and amineptine, a norepinephrine-dopamine disinhibitor such as agomelatine, a tricyclic antidepressant such as amitriptyline, clomipramine, doxepin, imipramine, trimipramine, desipramine, nortriptyline, protriptyline, a monoamine oxidase inhibitor such as isocarboxazid, moclobemide, phenelzine, selegiline, tranylcypromine.

In some embodiments, the disclosure relates to the use of a compound disclosed herein in the production of a medicament for the treatment or prevention of a BDNF and TrkB related disease or condition.

BRIEF DESCRIPTION OF THE DRAWINGS

FIG. 3B shows quantitative analysis of amyloid plaques for AD. Amyloid deposition in 5×FAD mice was significantly decreased by orally administrated CF3-CN.

FIG. 3C shows data indicating CF3-CN improves the spatial learning and memory of 5×FAD mice, i.e., improves the cognitive functions in 5×FAD mice. 5×FAD mice (n=8-10/group) orally administrated with control vehicle or different doses CF3-CN were trained in the water maze over five days. The area under curve of latency (AUC latency) compared to vehicle-treated 5×FAD mice.

FIG. 3D shows data on the percentage of time spent in target quadrant.

DETAILED DISCUSSION

Terms

Figure 1A:
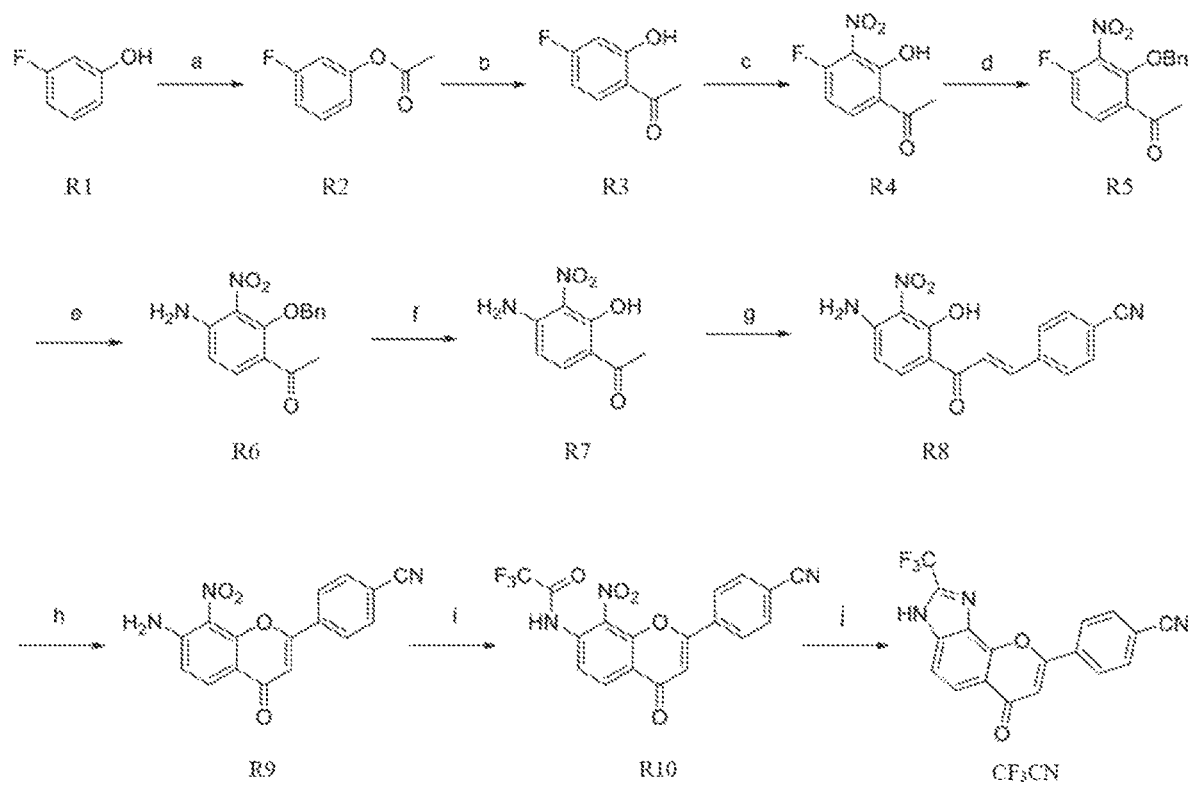
FIG. 1A illustrates the preparation of the compound designated CF3-CN with the chemical name 4-(6-oxo-2-(trifluoromethyl)-3,6-dihydrochromeno[7,8-d]imidazol-8-yl)benzonitrile. Reagents and conditions: (a) $Ac_2O$, pyridine, DCM, 0° C., 3 h; (b) $AlCl_3$, 180° C., 3 h; (c) $H_2SO_4$, $HNO_3$, 0° C., 30 min; (d) BnBr, $K_2CO_3$, ACN, 70° C., overnight; (e) DMSO, $NH_3 \cdot H_2O$, 50° C., 2 h; (f) DCM, $BBr_3$, rt, 2 h; (g) 4-formylbenzonitrile, DMF, NaH, rt, 5 h; (h) DMSO, $I_2$, 130° C., 1 h; (i) DMF, TFAA, r.t, 3 h; (j) MeOH, Fe, 50° C., overnight.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

With regard to chemical structure, it is understood that claiming compounds that are racemic encompasses all of the isomers, tautomers, enantiomers, or diastereomers unless otherwise specified to be a composition of excess of a specific isomer. For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers) such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to the total weight of the preparation, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

As used herein, the term "tautomer" is a type of isomer that includes two or more interconvertible compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base or can occur without the action or presence of an external agent. Exemplary tautomerizations include, but are not limited to, keto-enol; amide-imide; lactam-lactim; enamine-imine; and enamine-(a different) enamine tautomerizations. A specific example of keto-enol tautomerization is the interconversion of pentane-2,4-dione and 4-hydroxypent-3-en-2-one tautomers.

As used herein a "flavone" refers to any compound comprising a 2-phenyl-4H-chromen-4-one ring system.

As used herein, "alkyl" means a noncyclic straight chain or branched, unsaturated or saturated hydrocarbon such as those containing from 1 to 10 carbon atoms, typically 1 to 6 carbon atoms. Within any embodiments, herein alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), mono-cyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkyloxycarbonyl" refers to an alkyl as defined above attached through a carboxy bridge (i.e., —(C=O)Oalkyl.

"Alkylcarbamoyl" refers to an alkyl as defined above attached through a carbonyl bridge (i.e., —(C=O)NHalkyl).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above attached through a sulfamoyl bridge (i.e., —S(=O)$_2$NHalkyl), and an "Arylsulfonamide" refers to an alkyl attached through a sulfamoyl bridge (i.e., (i.e., —S(=O)$_2$NHaryl).

"Alkylsulfinyl" refers to an alkyl as defined attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulphur atom or replacing an amino group with a hydroxyl group. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

An "excipient" refers to an inert substance added to a pharmaceutical composition facilitating administration of a compound. Examples, without limitation, of excipients include calcium carbonate, calcium phosphate, various sugars and types of starch, cellulose derivatives, gelatin, vegetable oils and polyethylene glycols.

Compounds

In certain embodiments, the disclosure relates to compounds of Formula I:

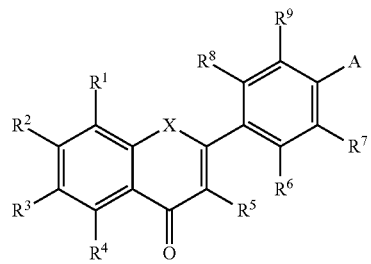

Formula I or salt, prodrug, or ester thereof wherein
X is O, S, or NH;
A is cyano (—CN);
$R^1$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^1$ is optionally substituted with one or more, the same or different, $R^{15}$; or $R^1$ and $R^2$ and attached atoms form a 5 membered heterocyclic ring, such as imidazolyl optionally substituted with $R^{15}$;
$R^2$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{15}$;
$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$ are optionally substituted with one or more, the same or different, $R^{15}$;
$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and
$R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is O.

In certain embodiments, $R^1$ and $R^2$ form imidazolyl or indolyl.

In certain embodiments, $R^7$ and $R^9$ are a halogen, one of or both.

In certain embodiments, $R^6$ and $R^8$ are a halogen, one of or both.

In certain embodiments, $R^4$ is a halogen, e.g., halogen is fluoro.

In certain embodiments, the disclosure relates to compounds of Formula IA or IC:

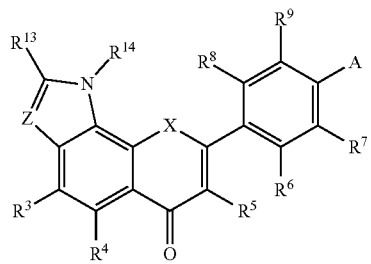

Formula IA

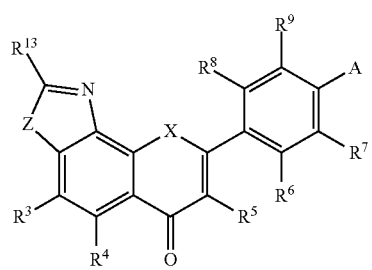

Formula IC or salt, prodrug, or ester thereof wherein
X is O, S, or NH;
A is cyano (—CN);
Z is N or NH;
$R^3$, $R^4$, $R^5$, $R^6$, $R^7$, $R^8$, $R^9$, $R^{13}$, and $R^{14}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, $R^9$, $R^{13}$, and $R^{14}$ are optionally substituted with one or more, the same or different, $R^{15}$;
$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and
$R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Z is NH and $R^{13}$ is alkyl optionally substituted with one or more halogens, e.g., trifluoromethyl.

In certain embodiments, Z is N wherein $R^{14}$ is absent in formula IC.

In certain embodiments, Z is N and $R^{13}$ is trifluoromethyl, wherein $R^{14}$ is absent in formula IC.

In certain embodiments, Z is N, $R^{13}$ is hydroxy, and $R^{14}$ is methyl.

In certain embodiments, $R^4$ is a halogen, e.g., halogen is fluoro.

In certain embodiments, $R^{13}$ is alkyl.

In certain embodiments, $R^{13}$ is hydroxy, and $R^{14}$ is alkyl, e.g., methyl.

In certain embodiments, the disclosure relates to compounds of Formula IB:

Formula IB or salt, prodrug, or ester thereof wherein

X is O, S, or NH;

A is cyano (—CN);

Z is N or CH;

$R^3$, $R^4$, $R^5$, $R^6$, $R^7$, $R^8$, and $R^9$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$, are optionally substituted with one or more, the same or different, $R^{15}$;

$R^{14}$ is alkyl;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of Formula IC:

Formula IC or salt, prodrug, or ester thereof wherein

X is O, S, or NH;

A is cyano (—CN);

Z is $NR^{14}$;

$R^3$, $R^4$, $R^5$, $R^6$, $R^7$, $R^8$, $R^9$, $R^{13}$, and $R^{14}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, $R^9$, $R^{13}$, and $R^{14}$ are optionally substituted with one or more, the same or different, $R^{15}$;

$R^{15}$ is independently selected alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to a compound selected from:

4-(1-methyl-2,6-dioxo-1,2,3,6-tetrahydrochromeno[7,8-d]imidazol-8-yl)benzonitrile or salts thereof, and 4-(6-oxo-2-(trifluoromethyl)-3,6-dihydrochromeno[7,8-d]imidazol-8-yl)benzonitrile or salts thereof.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids that form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier that releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, surfactants, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropyl methylcellulose, hydroxypropyl cellulose, ethylcellulose, and magnesium aluminum silicate, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, arginine, gums or cross-linked polymers, such as cross-linked PVP.

Stabilizers are used to inhibit or retard drug decomposition reactions which include, by way of example, oxidative reactions.

Surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine, and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the inhibitor(s) to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, M D, 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl celluloses such as hydroxypropyl cellulose, hydroxypropyl methylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, polymerized copolymers of acrylic and methacrylic acid esters with a low content of quaternary ammonium groups.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. In certain embodiments, the lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropyl methylcellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate vinyl polymers and copolymers such as polyvinyl pyrrolidone, vinyl acetate, vinyl acetate phthalate, vinyl acetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating and will generally represent about 10 wt % to 50 wt % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying and will generally represent approximately 25 wt % to 100 wt % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first-time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered in combination with other active compounds. These compounds include but are not limited to analgesics, anti-inflammatory drugs, antipyretics, antidepressants, antiepileptics, antihistamines, antimigraine drugs, antimuscarinics, anxiolytics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

Specific examples of compounds that can be adjunctively administered with the compounds include, but are not limited to, aceclofenac, acetaminophen, atomoxetine, almotriptan, alprazolam, amantadine, amcinonide, aminocyclopropane, amitriptyline, amlodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, rizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketanserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methyl salicylate, methysergide, metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprozin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propranolol, propizepine, propoxyphene, protriptyline, quazepam, quinupramine, reboxetine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenazine, thiazides, thioridazine, thiothixene, tiapride, buspirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

Methods of Use

In certain embodiments, the disclosure relates to methods of preventing or treating a BDNF and TrkB related disease or condition comprising the administering an effective amount of a pharmaceutical composition disclosed herein, to a subject in need thereof. In some embodiments, the subject is diagnosed with, exhibiting symptoms of, or at risk of the disease or condition. In some embodiments, the disease or condition is depression, anxiety, amyotrophic later sclerosis, Alzheimer's disease, Huntington's disease, Rett syndrome, epilepsy, Parkinson's disease, dementia, diabetic neuropathy, peripheral neuropathy, obesity, or stroke.

In certain embodiments, the methods described herein include a method of treating or reducing the risk of disorders associated with activation of the TrkB receptor including neurological disorders, neuropsychiatric disorders, and metabolic disorders in a subject. Examples of neurological and neuropsychiatric disorders include depression, anxiety, Alzheimer's, CNS injuries, and the like. Examples of metabolic disorders include obesity and hyperphagia. This method includes the steps of selecting a subject with or at risk of developing the neurological disorder, neuropsychiatric disorder, or obesity, and administering to the subject a therapeutically effective amount of a compound disclosed herein. The compound can be administered systemically (e.g., orally, parenterally (e.g. intravenously), intramuscularly, intraperitoneally, transdermally (e.g., by a patch), extracorporeally, topically, by inhalation, subcutaneously or the like), by administration into the central nervous system (e.g., into the brain (intracerebrally or intraventricularly), spinal cord, or into the cerebrospinal fluid), or any combination thereof.

In certain embodiments, the methods described herein include a method of improving memory, e.g., in a subject diagnosed with a dementia or related disorder.

The subject in need thereof can be a patient diagnosed as suffering from depression or anxiety. These diseases and their diagnoses are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. In certain embodiments, the patient is being administered an antidepressant or anti-anxiolytic medication. In certain embodiments, the patient has been diagnosed by a mental health professional (e.g., a psychiatrist) with an anxiety or depression disorder. Anxiety can be a symptom of an underlying health issue such as chronic obstructive pulmonary disease (COPD), heart failure, or heart arrhythmia.

The subject in need thereof can be a patient diagnosed as suffering from being overweight or obese. Being overweight and obesity can be diagnosed by health or nutritional professionals (e.g., physicians, nurses, dieticians, and the like) when the patient's body mass index (BMI), a measurement which compares weight and height, is between 25 kg/m and 30 kg/m$^2$, and obese when it is greater than 30 kg/m$^2$.

Also provided is a method of promoting neuroprotection in a subject. This method includes the steps of selecting a subject in need of neuroprotection and administering to the subject a therapeutically effective amount of a compound disclosed herein. A subject in need of neuroprotection can be a subject that has amyotrophic lateral sclerosis (ALS) or a central nervous system injury. A central nervous system injury includes, for example, a brain injury, a spinal cord injury, or a cerebrovascular event (e.g., a stroke). Methods can further comprise testing the effectiveness of a compound disclosed herein. Testing the effectiveness can include, but is not limited to, imaging (e.g., Magnetic Resonance Imaging (MRI)) and functional measurements (e.g., survival or clinical symptoms like analysis of speech patterns, logic, comprehension, memory, mood, and orientation).

EXAMPLES

Preparation of CF3CN (FIG. 1A)

Figure 1B:
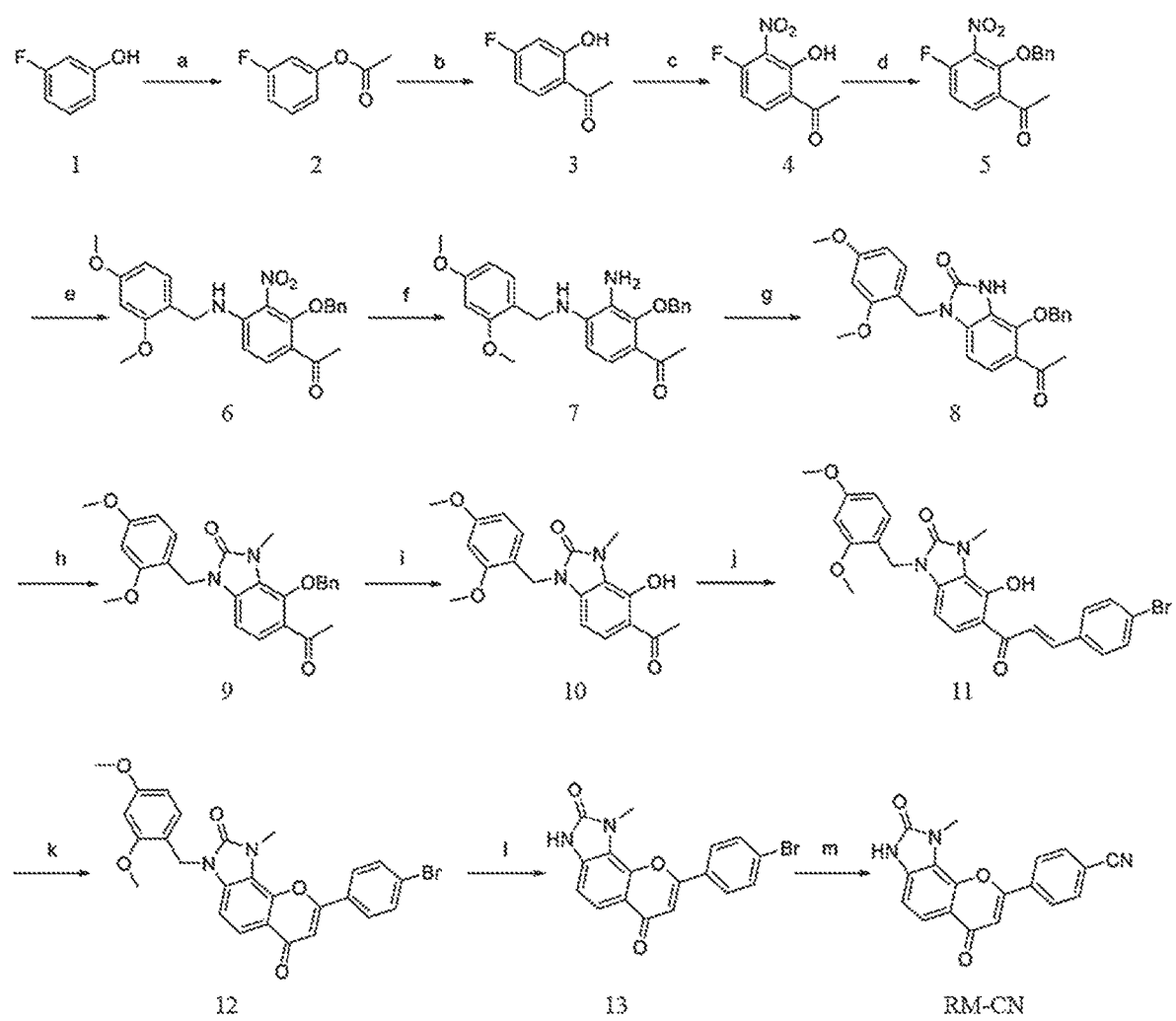
FIG. 1B illustrates the preparation of the compound designated RM-CN with the chemical name 4-(1-methyl-2,6-dioxo-1,2,3,6-tetrahydrochromeno[7,8-d]imidazol-8-yl)benzonitrile. Reagents and conditions: (a) $Ac_2O$, pyridine, DCM, 0° C., 3 h; (b) $AlCl_3$, 180° C., 3 h; (c) $H_2SO_4$, $HNO_3$, 0° C., 30 min; (d) BnBr, $K_2CO_3$, ACN, 70° C., overnight; (e) $DMBNH_2$, DMF, r.t., 3 h; (f) $Na_2S_2O_4$, EtOH, reflux, overnight; (g) CDI, THF, r.t., 3 h; (h) $CH_3I$, $K_2CO_3$, DMF, 80° C., overnight; (i) 20% Pd(OH)$_2$/C, $H_2$, r.t., overnight; U) 4-bromobenzaldehyde, NaH, THF, r.t., overnight; (k) $I_2$, DMSO, 130° C., 2 h; (l) TfOH, toluene, 140° C., overnight; (m) $Zn(CN)_2$, triphenylphosphine, palladium acetate, 140° C., overnight.

The preparation of this compound is illustrated in FIG. 1B.

R2—To a solution of R 1 (200 g, 1.57 mol) in DCM (2 L) was added pyridine (155 g, 1.96 mol), Ac$_2$O (200 g, 1.96 mol) at 0° C. The mixture was stirred at 0° C. for 3 hrs. Ice-water (2 L) was added. The mixture was extracted with DCM (1000 mL×2), the combined organic layer was washed with brine, dried over Na$_2$SO$_4$ and evaporated in vacuum to give R2 (190 g, yield 69%) as a red oil. $^1$H NMR (CDCl$_3$, 400 MHz): δ (ppm) 2.29 (s, 3H), 6.84-6.96 (m, 3H), 7.29-7.37 (m, 1H).

R3—A mixture of R2 (190 g, 1.23 mol) and AlCl$_3$ (295 g, 2.22 mol) was stirred at 180° C. for 3 h under N2 atmosphere. The mixture was cooled to room temperature and was added cold water (1 L), extracted with DCM (1000 mL×2). The combined organic layer was washed with brine (1000 mL), dried over Na$_2$SO$_4$ and evaporated in vacuum to give the crude product which was purified by column chromatography on silica gel to give R3 (104 g, yield 67.5%) as a white solid. $^1$H NMR (CDCl$_3$, 400 MHz): δ (ppm) 2.62 (s, 3H), 6.63-6.69 (m, 2H), 7.73-7.79 (m, 1H), 12.60 (s, 1H).

R4—To a solution of conc. H$_2$SO$_4$ (400 mL) was added R3 (100 g, 0.65 mmol) at 0° C. Conc. HNO$_3$ (66 mL) was added to the mixture dropwise at 0° C. during 30 min. After addition, ice-water (2 L) was added. The mixture was extracted with EtOAc (500 mL×2). The combined organic layer was washed with brine (1000 mL), dried over Na$_2$SO$_4$ and evaporated in vacuum to give the residue which was purified by column chromatography on silica gel (eluent: petroleum ether/ethyl acetate=10/1-3/1) to give R 7 (45 g, yield 35%) as a yellow solid. $^1$H NMR (CDCl$_3$, 400 MHz): δ (ppm) 2.67 (s, 3H), 6.77-6.83 (t, J=9.0 Hz, 1H), 7.90-7.95 (dd, J=9.0, 6.3 Hz, 1H), 13.30 (s, 1H).

R5—A solution of R4 (10 g, 0.05 mol), K$_2$CO$_3$ (13.8 g, 0.1 mol), BnBr (9.35 g, 0.055 mol) in ACN (100 mL) was stirred at 70° C. overnight. The mixture was concentrated and then diluted with water (100 mL). The mixture was extracted with EtOAc (100 mL×2). The combined organic layer was washed with water (200 mL), brine (200 mL), dried over Na$_2$SO$_4$ and evaporated in vacuum to give R5 (6 g, yield 41.4%) as yellow solid. $^1$H NMR (CDCl$_3$, 400

MHz): δ (ppm) 2.56 (s, 3H), 5.06 (s, 2H), 7.08-7.11 (t, J=8.7 Hz, 1H), 7.36-7.41 (m, 5H), 7.77-7.82 (dd, J=9.0, 6.3 Hz, 1H).

R6—To a solution of R5 (10 g, 34.6 mmol) in DMSO (50 mL) was added NH$_3$·H$_2$O dropwise at r.t. The reaction was stirred at 50° C. for 1 hr. The mixture was poured into water (60 mL) and extracted with EtOAc (50 mL×2). The combined organic layer was washed with water (100 mL×3), brine (100 mL×2), dried over Na$_2$SO$_4$ and filtered. The filtrate was concentrated to give crude R6 (7.2 g, yield 83.6%) as a red oil.
$^1$H NMR (CDCl$_3$, 400 MHz): δ (ppm) 2.52 (s, 3H), 5.00 (s, 2H), 5.35 (s, 2H), 6.58-6.60 (d, J=8.8 Hz, 1H), 7.37-7.44 (m, 5H). 7.69-7.70 (d, J=8.8 Hz, 1H).

R7—To the solution of R6 (8 g, 28 mmol) in DCM (80 mL) was added boron tribromide dropwise at −78° C. The reaction was stirred at rt. for 2 hrs. MeOH was added to above mixture dropwise at 0° C. The reaction was diluted with water (100 mL) and extracted with EtOAc (50 mL×2). The organic layer was washed with water (100 mL), brine (100 mL), dried over Na$_2$SO$_4$, concentrated in vacuum to give crude product which was triturated with EtOAc to give R 7 (3 g, yield 37%) as a yellow solid. $^1$H NMR (CDCl3, 400 MHz): δ (ppm) 2.70 (s, 3H), 8.01-8.04 (d, J=12.2 Hz, 2H).

R8—To a solution of R7 (3 g, 15.3 mmol) in DMF (30 mL) was added NaH (1.8 g, 45.9 mmol) batchwise at 0° C., the mixture was stirred at room temperature for 0.5 hrs. The solution of 4-formylbenzonitrile (3.93 g, 30 mmol) in DMF (5 mL) was added to above solution dropwise at 0° C. The mixture was stirred at r.t for 3 hrs. The mixture was quenched with water and filtered, the filtrate cake was dried in vacuum to give R8 (2.2 g, yield 49%) as a yellow solid.
$^1$H NMR (CDCl3, 400 MHz): δ (ppm) 6.49-6.52 (d, J=9.2 Hz, 1H), 7.68 (s, 2H), 7.82-7.86 (d, J=15.2 Hz, 1H), 7.93-7.95 (d, J=8 Hz, 2H), 8.07-8.12 (m, 3H), 8.23-8.25 (d, J=9.2 Hz, 1H).

R9—To a solution of compound R8 (2.2 g, 7.12 mmol) in DMSO (10 mL) was added 12 (270 mg, 1.07 mmol) in one batch. The mixture was stirred at 130° C. for 1 hr. The mixture was cooled to room temperature, quenched with ice-water (100 mL). The precipitate was filtered, the filtrate cake was triturated with MeOH (10 mL×2) to give R9 (1.1 g, yield 50%) as a yellow solid. $^1$H NMR (CDCl3, 400 MHz): δ (ppm) 6.99-7.02 (d, J=9.2 Hz, 1H), 7.23 (s, 1H), 7.87-7.90 (d, J=9.2 Hz, 2H), 8.07-8.09 (d, J=8.8 Hz, 2H), 8.21-8.23 (d, J=8.8 Hz, 2H).

R$^{10}$—To a mixture of compound R9 (500 mg, 1.63 mmol) in pyridine (10 mL) was added TFAA (1.03 g, 4.89 mmol) dropwise at 0° C., the mixture was stirred at room temperature for 2 hrs. The mixture was diluted with water (10 mL) and extracted with EtOAc (10 mL×2). The organic layer was washed with HCl (0.5 M, 10 mL), brine (100 mL), dried over Na$_2$SO$_4$, concentrated in vacuum to give R10 (405 mg, yield 66.7%) as a yellow solid. $^1$H NMR (CDCl$_3$, 400 MHz): δ (ppm) 7.38 (s, 1H), 7.74-7.76 (d, J=8.4 Hz, 1H), 8.09-8.17 (m, 4H), 8.28-8.30 (d, J=8.8 Hz, 1H).

CF3CN—To a solution of R10 (405 mg, 1.09 mmol) and Fe (304 mg, 5.4 mmol) in MeOH (10 mL) was added HAc (5 mL) in portions. The mixture was stirred at 50° C. for 2 hrs. The mixture was filtered; the filtrate was poured into water (20 mL) and extracted with EtOAc (20 mL×2). The combined organic layer was washed with water (20 mL×2), brine (20 mL×2), dried over Na$_2$SO$_4$ and filtered. The filtrate was concentrated to give crude product which was purified by prep-HPLC to give CF3CN (300 mg, yield 77.9%) as a yellow solid. $^1$H NMR (DMSO_d$_6$, 400 MHz): δ (ppm) 7.33 (s, 1H), 7.75-7.77 (d, J=8.8 Hz, 1H), 7.98-8.00 (d, J=8.8 Hz, 1H), 8.10-8.12 (d, J=8.4 Hz, 2H), 8.37-8.39 (d, J=7.6 Hz, 2H); >98% at 220 nm, MS (ESI) m/z=356.1 [M+H]+.

Preparation of RM-CN (FIG. 1B)

To a solution of compound 1 (300 g, 2.68 mol) in DCM (3 L) was added pyridine (234 g, 2.94 mol), Ac$_2$O (300 mL, 2.94 mol) at 0° C. and the mixture was stirred at 0° C. for 3 h. Ice-water (3 L) was added. The mixture was extracted with DCM (1000 mL×2), the combined organic layer was washed with brine, dried over Na$_2$SO$_4$ and evaporated in vacuum to give compound 2 (420 g, yield 100%) as a red oil.
$^1$H NMR (CDCl3, 400 MHz): δ (ppm) 2.29 (s, 3H), 6.84-6.96 (m, 3H), 7.29-7.37 (m, 1H).

Compound 3—A mixture of compound 2 (420 g, 2.72 mol) and AlCl$_3$ (651 g, 4.89 mol) was stirred at 180° C. for 3 h under N$_2$ atmosphere. The mixture was cooled to room temperature and was added cold water (1 L), extracted with DCM (1000 mL×2). The combined organic layer was washed with brine (1000 mL), dried over Na$_2$SO$_4$ and evaporated in vacuum to give the crude product which was purified by column chromatography on silica gel to give compound 3 (290 g, yield 69%) as a white solid.
$^1$H NMR (CDCl3, 400 MHz): δ (ppm) 2.62 (s, 3H), 6.63-6.69 (m, 2H), 7.73-7.79 (m, 1H), 12.60 (s, 1H).

Compound 4—To a solution of conc. H$_2$SO$_4$ (260 mL) was added compound 3 (65 g, 0.42 mmol) at 0° C. Conc. HNO$_3$ (33 mL) was added to the mixture dropwise at 0° C. during 30 min. After addition, ice-water (700 mL) was added. The mixture was extracted with EtOAc (500 mL×2). The combined organic layer was washed with brine (1 L), dried over Na$_2$SO$_4$ and evaporated in vacuum to give the residue which was purified by column chromatography on silica gel (eluent: petroleum ether/ethyl acetate=10/1-3/1) to give compound 4 (33 g, yield 39.76%) as a yellow solid. $^1$H NMR (CDCl3, 400 MHz): δ (ppm) 2.67 (s, 3H), 6.77-6.83 (t, J=9.0 Hz, 1H), 7.90-7.95 (dd, J=9.0, 6.3 Hz, 1H), 13.30 (s, 1H).

Compound 5—A solution of compound 4 (140 g, 0.7 mol), K$_2$CO$_3$ (193 g, 1.39 mol), BnBr (132 g, 0.77 mol) in ACN (1500 mL) was stirred at 70° C. overnight. The mixture was concentrated and then diluted with water (1000 mL). The mixture was extracted with EtOAc (1000 mL×2). The combined organic layer was washed with water (500 mL), brine (500 mL), dried over Na$_2$SO$_4$ and evaporated in vacuum to give compound 5 (110 g, yield 54%) as yellow solid. $^1$H NMR (CDCl$_3$, 400 MHz): δ (ppm) 2.56 (s, 3H), 5.06 (s, 2H), 7.08-7.11 (t, J=8.7 Hz, 1H), 7.36-7.41 (m, 5H), 7.77-7.82 (dd, J=9.0, 6.3 Hz, 1H).

Compound 6—A solution of compound 5 (30 g, 103 mmol) and (2,4-dimethoxyphenyl) methanamine (27.6 g, 166 mmol) in DMF (300 mL) was stirred at room temperature for 3 hrs. The mixture was poured into water (600 mL) and then extracted with EtOAc (400 mL×2). The combined organic layer was washed with water (500 mL), brine (500 mL), dried over Na$_2$SO$_4$ and filtered. The filtrate was concentrated to give crude compound 6 (45 g) as a red oil.

Compound 7—The solution of compound 6 (45 g, 103 mmol), Na$_2$S$_2$O$_4$ (538 g, 3090 mmol) in EtOH (300 mL) and water (200 mL) was stirred to reflux overnight. The mixture was cooled to room temperature and concentrated in vacuum. The residue was diluted with water (300 mL) and extracted with EtOAc (300 mL×2). The organic layer was washed with water (500 mL), brine (500 mL), dried over Na$_2$SO$_4$, concentrated in vacuum to give crude product which was triturated with EtOAc to give compound 7 (15 g, yield 34%) as a yellow solid. $^1$H NMR (CDCl$_3$, 400 MHz):

δ (ppm) 2.58 (s, 3H), 3.83 (s, 3H), 3.86 (s, 3H), 4.33 (s, 2H), 4.91 (s, 2H), 6.46-6.53 (m, 3H), 7.18-7.20 (d, 1H), 7.35-7.51 (m, 6H).

Compound 8—A solution of compound 7 (10 g, 24.6 mmol), CDI (16.8 g, 110.84 mmol) and TEA (7.46 g, 73.8 mmol) in THF (100 mL) was stirred at room temperature for 3 hrs. The mixture was diluted with water (200 mL) and extracted with EtOAc (100 mL×2). The combined organic layer was washed with water (200 mL), brine (200 mL), dried over $Na_2SO_4$, concentrated in vacuum to give compound 8 (10.5 g, yield 100%) as a white solid. $^1$H NMR ($CDCl_3$, 400 MHz): δ (ppm) 2.60 (s, 3H), 3.83 (s, 3H), 3.71-3.77 (m, 2H), 3.77 (s, 3H), 3.86 (s, 3H), 5.01 (s, 2H), 5.13 (s, 2H), 6.35-6.38 (t, 1H), 6.46-6.47 (d, 1H), 6.85-6.87 (d, 1H), 7.11-7.14 (d, 1H), 7.36-7.37 (t, 3H), 7.49-7.54 (m, 3H), 9.85 (s, 1H).

Compound 9—To a mixture of compound 8 (9.5 g, 21.2 mmol) and $K_2CO_3$ (6.1 g, 44.2 mmol) in DMF (100 mL) was added $CH_3I$ (3.5 g, 24.6 mmol) dropwise at room temperature. The mixture was stirred at 80° C. overnight. The mixture was diluted with water (200 mL) and extracted with EtOAc (100 mL×2). The combined organic layer was washed with water (200 mL), brine (200 mL), dried over $Na_2SO_4$, concentrated in vacuum to give the residue which was purified by column chromatography on silica gel (eluent: petroleum ether/ethyl acetate=10/1-3/1) to give compound 12 (9 g, yield 92.0%) as a white solid. $^1$H NMR ($CDCl_3$, 400 MHz): δ (ppm) 2.60 (s, 3H), 3.48 (s, 3H), 3.77 (s, 3H), 3.85 (s, 3H), 4.96 (s, 2H), 5.02 (s, 2H), 6.42-6.47 (m, 2H), 6.90-6.92 (d, 1H), 7.19-7.28 (d, 1H), 7.40-7.46 (m, 6H).

Compound 10—A mixture of compound 9 (8 g, 17.9 mmol) and $Pd(OH)_2/C$ (2.0 g, 20%) in MeOH (90 mL) and water (23 mL) was stirred at room temperature for 50 min under $H_2$ atmosphere. The mixture was filtered, and the filtrate was concentrated in vacuum to give compound 10 (6 g, yield 94%) as a white solid $^1$H NMR ($CDCl_3$, 400 MHz): δ (ppm) 2.60 (s, 3H), 3.74-3.78 (d, 6H), 3.86 (s, 3H), 5.02 (s, 2H), 6.45-6.46 (d, 2H), 6.61-6.63 (d, 1H), 7.15 (s, 1H), 7.42-7.44 (d, 1H), 12.94 (s, 1H).

Compound 11—To a solution of compound 10 (6 g, 16.85 mmol) and NaH (1.68 g, 42.mmol) in DMF (60 mL) was added 4-bromobenzaldehyde (9.4 g, 50.8 mmol) in portion. The mixture was stirred at room temperature overnight. The mixture was extracted with EtOAc (100 mL×2). The combined organic layer was washed with water (100 mL), brine (100 mL), dried over $Na_2SO_4$, concentrated in vacuum to give the crude product which was triturated with EtOAc (20 mL×2) to give compound 11 (6 g, yield 68%) as a yellow solid. $^1$H NMR (DMSO-$d_6$, 400 MHz): δ (ppm) 3.60 (s, 3H), 3.72 (s, 3H), 3.83 (s, 3H), 4.95 (s, 2H), 6.45-6.47 (d, 1H), 6.59 (s, 1H), 6.76-6.78 (d, 1H), 6.97-6.99 (d, 1H), 7.67-7.69 (d, 2H), 7.79-7.83 (d, 1H), 7.88-7.90 (d, 2H), 8.08-8.12 (m, 3H).

Compound 12—To a solution of compound 11 (6 g, 11.5 mmol) in DMSO (100 mL) was added 12 (437 mg, 1.72 mmol). The mixture was stirred at 130° C. for 2 hours. The mixture was cooled to room temperature, quenched with ice-water (100 mL). The precipitate was filtered, the filtrate cake was triturated with MeOH (10 mL×2) to give compound 12 (5 g, yield 83%) as a brown solid.

Compound 13—To a solution of compound 12 (5 g, 9.61 mmol) in toluene (50 mL) was added TfOH (50 mL). The mixture was stirred at 140° C. overnight. The mixture was cooled to room temperature, then ice-water (5 mL) was added. The mixture was extracted with EtOAc (50 mL×2), and the organic layer was washed with water (50 mL), brine (50 mL), concentrated in vacuum to give crude product, which was triturated with EtOAc (10 mL×2) to give compound 13 (2.5 g, yield 71%) as a brown solid. $^1$H NMR (DMSO-$d_6$, 400 MHz): δ (ppm) 3.73 (s, 3H), 6.99 (s, 1H), 7.15-7.17 (d, 1H), 7.69-7.71 (d, 1H), 7.79-7.81 (d, 2H), 7.98-8.00 (d, 2H).

RM-CN To a solution of compound 13 (500 mg, 1.34 mmol) in DMF (10 mL) was added $Zn(CN)_2$ (313.6 mg, 2.68 mmol), triphenylphosphine (52 mg, 0.2 mmol) under $N_2$, the mixture was stirred at room temperature for 5 min. Then palladium acetate (44.8 mg, 0.2 mmol) was added to above solution under $N_2$ atmosphere and the mixture was stirred at 140° C. overnight. The mixture was cooled to room temperature, quenched with water (100 mL). The precipitate was filtered, the filtrate cake was triturated with EA (10 mL×2) to give RM-CN (400 mg, yield 93%) as a brown solid. $^1$H NMR ($CF_3COOD$, 400 MHz): δ (ppm) 4.14 (s, 3H), 7.78-7.83 (m, 2H), 8.06-8.08 (d, 2H), 8.28-8.35 (m, 3H), >90% at 220 nm, MS (ESI) m/z=318 [M+H]+.

In Vitro Testing of RM-CN and CF3CN

Based on in vitro plasma, hepatocyte and liver microsomal stability assays, CF3-CN was more stable than RM-CN. Both compounds are brain permeable absorb through the intestine. CF3-CN is more water soluble than RM-CN. In vitro TrkB activation assays on TrkB stable transfected T48 and primary neuronal cultures, both compounds display comparable $EC_{50}$ in triggering TrkB receptor activation.

| BBB-PAMPA Permeability: Data Summary | | | |
|---|---|---|---|
| Test Article | Pe | Recovery (%) | Test Conc. |
| Atenolol | NC | 84.6% | 10 μM |
| Verapamil | 2.13 | 26.3% | 10 μM |
| CF3-CN | 3.09 | 89.9% | 10 μM |
| RM-CN | 2.82 | 71.0% | 1 μM |
| z257 | 1.63 | 30.1% | 10 μM |
| z644 | 2.16 | 13.5% | 10 μM |

| Plasma Stability: Half-Life Data Summary | | | | |
|---|---|---|---|---|
| Compound | Species | Half Life (min) | MRM Transition | Avg % Remaining at Last Point* |
| CF3-CN | Human | >480 | 356.01 > 153.891 | 94.2 |
| Propantheline | Human | 23.9 | 369.315 > 182.078 | 3.15 |
| RM-CN | Human | >480 | 317.98 > 153.858 | 91.1 |
| Warfarin | Human | >480 | 309.149 > 163.011 | 93.6 |
| CF3-CN | Mouse | >480 | 356.01 > 153.891 | 107 |
| Propantheline | Mouse | 22.2 | 369.315 > 182.078 | 2.56 |
| RM-CN | Mouse | 345 | 317.98 > 153.858 | 80.3 |
| Warfarin | Mouse | 327 | 309.149 > 163.011 | 80.8 |

| Microsomal Intrinsic Clearance: Data Summary | | | | | |
|---|---|---|---|---|---|
| Test Article | Test Species | NADPH-dependent $CL_{int}{}^a$ (μl/min/mg) | NADPH-dependent $T_{1/2}{}^b$ (min) | NADPH-free $CL_{int}{}^a$ (μl/min/mg) | NADPH-free $T_{1/2}{}^b$ (min) |
| CF3-CN | Human | <12.8 | >180 | <12.8 | >180 |
| RM-CN | Human | 30.3 | 76.2 | <12.8 | >180 |
| Midazolam | Human | 511 | 4.52 | <12.8 | >180 |
| Verapamil | Human | 142 | 16.3 | <12.8 | >180 |

Microsomal Intrinsic Clearance: Data Summary

| Test Article | Test Species | NADPH-dependent CL$_{int}{}^a$ (μl/min/mg) | NADPH-dependent T$_{1/2}{}^b$ (min) | NADPH-free CL$_{int}{}^a$ (μl/min/mg) | NADPH-free T$_{1/2}{}^b$ (min) |
|---|---|---|---|---|---|
| CF3-CN | Mouse | <12.8 | >180 | <12.8 | >180 |
| RM-CN | Mouse | 231 | 10.0 | <12.8 | >180 |
| Midazolam | Mouse | 1099 | 2.10 | <12.8 | >180 |
| Verapamil | Mouse | 247 | 9.34 | <12.8 | >180 |

Hepatocyte Stability: Data Summary

| Compound | Species | Clearance (μl/min/million cells) | Half Life (min) | MRM Transition | Avg % Remaining at Last Point* |
|---|---|---|---|---|---|
| CF3-CN | Human | <2.9 | >480 | 356.01 > 153.891 | 97.2 |
| RM-CN | Human | 10.5 | 133 | 317.98 > 153.858 | 54.8 |
| 7-OH-Coumarin | Human | 88.5 | 15.7 | 229.061 > 152.96 | 7.17 |
| Midazolam | Human | 38.8 | 35.7 | 326.121 > 291.203 | 9.82 |
| Verapamil | Human | 62.3 | 22.3 | 455.305 > 150.075 | 2.40 |
| CF3-CN | Mouse | <2.9 | >480 | 356.01 > 153.891 | 94.8 |
| RM-CN | Mouse | 5.04 | 275 | 317.98 > 153.858 | 67.1 |
| 7-OH-Coumarin | Mouse | 63.2 | 21.9 | 229.061 > 152.96 | 38.8 |
| Midazolam | Mouse | 35.1 | 39.4 | 326.121 > 291.203 | 34.0 |
| Verapamil | Mouse | 31.0 | 44.8 | 455.305 > 150.075 | 41.0 |

CF3-CN and RM-CN compounds were testes for whether they could selectively stimulate TrkB activation in rat TrkB stably transfected SN56 cells (T48) that originally lack TrkB expression. The cells were treated with different doses of compounds for 15 min. Immunoblotting analysis demonstrated that CF3-CN activated both p-TrkB 706 and 816 in a dose-dependent way with EC$_{50}$ of 21.63 nM. However, RM-CN appears activated p-TrkB 706 gradually, whereas its effects on p-TrkB 816 behaved inversely, though p-Akt/p-MAPK downstream signals increased in a dose-dependent manner.

Cytoprotective effects were tested. To examine whether these compounds protect cells from staurosporine (STS)-induced apoptosis, MTT assays were conducted using TrkB stable transfected cells or TrkB deficient SN56 cells. Noticeably, both compounds strongly protected T48 cells from apoptosis with EC$_{50}$ of 26.7 and 12.5 nM, respectively. By contrast, these compounds exhibited weaker protective effects in TrkB lacking SN56 cells.

Endogenous TrkB activation in primary neurons were tested in DIV13 primary cortical cultures. The neurons were treated with the two compounds with doses for 15 min. The lysates were analyzed by immunoblotting with antibodies. Both RM-CN and CF3-CN displayed a dose-dependent effect in triggering TrkB activation, fitting with the downstream p-Akt/p-MAPK oscillation.

In Vivo Testing of CF3CN

The compounds were orally administered into wild-type mice or 3×Tg, an Alzheimer's disease (AD) mouse model. Both compounds induce dose-dependent TrkB neurotrophic signaling in the mouse brain. In vivo PK profiles of CF3-CN were tested after dosing CF3-CN in three ICR mice at 5 mg/kg. Blood samples were collected from three animals after oral administration at each designated time point (15 and 30 min, and 1, 2, 4, 8, 24 h). Concentration of CF3-CN in all mice plasma samples were determined by LC-MS/MS. Pharmacokinetic analysis was performed using non-compartmental methods. Following a single oral administration of CF3-CN at a dose of 5 mg/kg, the Cmax and Tmax values for CF3-CN were 11268 ng/ml and 49.8 min, respectively. The mean area under the curve (AUC)(0-t) value was 68533.8 hr ng/ml.

IV injection were delivered in twelve ICR mice at 2 mg/kg of CF3-CN for in vivo PK/BBB study. Blood samples were drawn from three animals after IV injection at each designated time point (4.8, 15 and 30 min, 1, 2, 4, 8, 24 h) and monitor CF3-CN concentration in all plasma by LC-MS/MS. Brain samples were harvested from three mice after IV injection at 1, 2, 4 h and CF3-CN concentration were measured in all brains. The concentration ratio of brain/plasma was calculated, and PK analysis was performed using a non-compartmental method. Following a single IV injection at 2 mg/kg, the Cmax value for CF3-CN reached 12747.9 ng/ml within 5 min (Tmax=4.8 min) in plasma sample, while in brain samples, the Cmax and Tmax were 63.3 ng/g and 1 h, respectively.

Plasma&Brain Concentrations (ng/ml, ng/g) of CF3-CN in Male ICR Mouse After 2 mg/kgIV Dosed

| Time point (h) | Animal Study No. | Plasma (ng/mL) | Brain (ng/g) | B/P Ratio |
|---|---|---|---|---|
| 1.00 | 1 | 4395.9 | 107.4 | 0.02 |
|  | 2 | 5962.7 | 48.0 | 0.01 |
|  | 3 | 5506.9 | 33.6 | 0.01 |
|  | Mean | 5288.5 | 63.0 | 0.01 |
|  | SD | 805.9 | 39.1 | 0.01 |
| 2.00 | 4 | 2471.4 | 22.8 | 0.01 |
|  | 5 | 1499.7 | 21.0 | 0.01 |
|  | 6 | 2492.4 | 27.0 | 0.01 |
|  | Mean | 2154.5 | 23.6 | 0.01 |
|  | SD | 567.2 | 3.1 | 0.00 |
| 4.00 | 7 | 519.9 | BLQ | NA |
|  | 8 | 594.1 | 9.6 | 0.02 |
|  | 9 | 520.4 | BLQ | NA |
|  | Mean | 544.8 | 9.6 | 0.02 |
|  | SD | 42.7 | NA | NA |

To explore whether chronic oral administration of CF3-CN can activate TrkB in mouse brain, 5×FAD mice were fed CF3-CN (3 mg/kg) or vehicle, beginning at 3 months of age. After 3 months of drug treatment, TrkB activation was monitored in the mouse brain by immunofluorescence with anti-phosphorylated TrkB (p-TrkB) antibody. Immunoblotting analysis revealed that the TrkB was markedly activated in CF3-CN-treated 5×FAD mice. Quantitative analysis revealed that p-TrkB signals but not total TrkB level were notably elevated upon CF3-CN treatment. TrkB receptors were more prominently phosphorylated in 5×FAD mice treated by CF3-CN than vehicle control, so were the downstream AKT and ERK/MAPK pathways. The signals were upregulated in a dose-dependent manner. This result was also confirmed in the hippocampus in CF3-CN-treated 5×FAD mice by immunofluorescence staining with anti-p-TrkB Y816. Given the fact that CF3-CN can pass the blood-brain barrier, these results indicate that chronic oral administration of CF3-CN activates TrkB receptor and its downstream signaling pathways in the brain. At the dose of 3 mg/kg, CF3-CN provoked TrkB activation in the hippocampus.

Repeated Oral Administration of CF3-CN Prevents Synaptic Loss in 5×FAD Mice

Figure 2A:
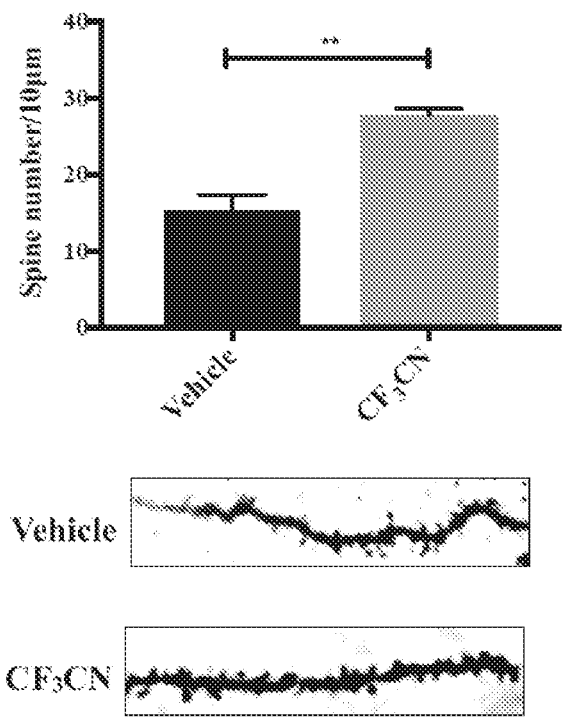
FIG. 2A shows data indicating CF3-CN prevents or reverses the synaptic loss in hippocampus of 5×FAD mice. The dendritic spines from apical dendritic layer of the CA1 region were analyzed by Golgi staining. (Scale bar, 5 m). On top is quantitative analysis of the spine density.
Figure 2B:
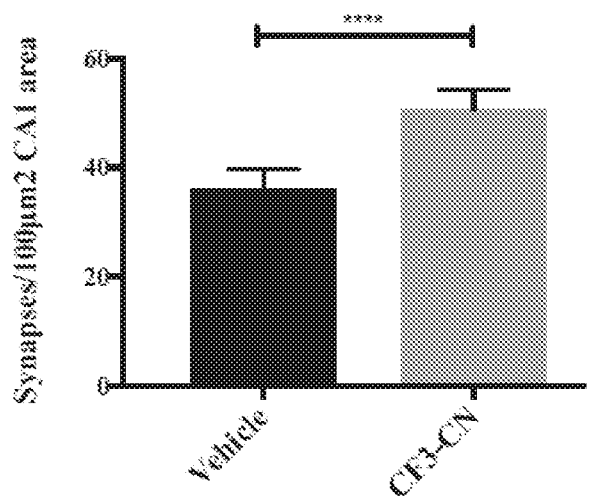
FIG. 2B shows quantitative analysis of the synaptic density in vehicle and CF3-CN-treated 5×FAD mice. 5×FAD mice show decreased synaptic density, which was reversed by CF3-CN.
Figure 2C:
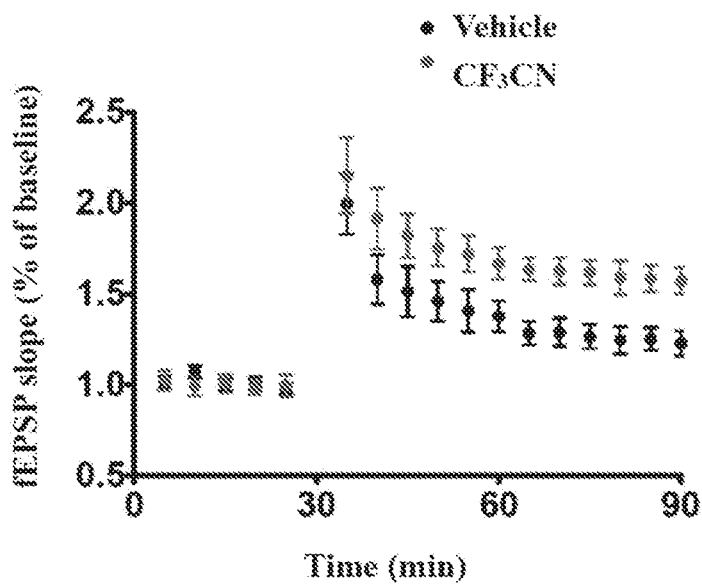
FIG. 2C shows data on LTP of field excitatory postsynaptic potential (fEPSPs) was induced by 3×TBS (theta-burst-stimulation) (four pulses at 100 Hz, repeated three times with a 200-ms interval). Shown traces are representative fEPSPs recorded at the time point 1 (vehicle-treated 5×FAD) and 2 (CF3-CN-treated 5×FAD mice). The magnitude of LTP in 5×FAD mice is significantly lower in vehicle transgenic mice, and CF3-CN treatment reversed the LTP impairment. (n=5 in each group. Data are presented as mean±SEM.*$p<0.05$, vehicle vs CF3-CN treated mice).

Synaptic loss is believed to be the basis of cognitive impairment in the early phase of Alzheimer's disease. In 5×FAD model, significant synaptic loss and behavior deficit are detected at 5 months old, when there is no detectable neuronal loss. The density of dendritic spines along individual dendrites of pyramidal neurons were assessed by Golgi staining. The density of dendritic spines was markedly decreased in 5×FAD mice model compared with non-transgenic group. Interestingly, the decrease of spine density was noticeably rescued by CF3-CN treatment (FIG. 2A). Since one dendritic spine can form more than one synapse, the densities of synapse in the CA1 area were quantified in 5×FAD mice brain by electron microscopy. 5×FAD mice showed a significant reduction in synaptic density. CF3-CN treatment remarkably reversed the loss of synaptic density in a dose-dependent way (FIG. 2B). Immunoblotting was done using pre-synaptic markers (synaptotagmin) and post-synaptic markers (GluR1, PSD95 and spinophilin). 5×FAD mice displayed a considerable decrease in these synaptic markers, indicating synaptic degeneration. CF3-CN treatment reversed the reduction of synaptic markers. Electrophysiology analysis demonstrated that CF3-CN treatment increased LTP (long-term potentiation), fitting with the findings of augmentation of synapses by CF3-CN. These results suggest that the activation of TrkB receptor by CF3-CN inhibits the loss of synapse in 5×FAD mice and improves synaptic plasticity.

CF3-CN Alleviates AP Deposition and Rescues Memory Deficits in 5×FAD Mice

Figure 3A:
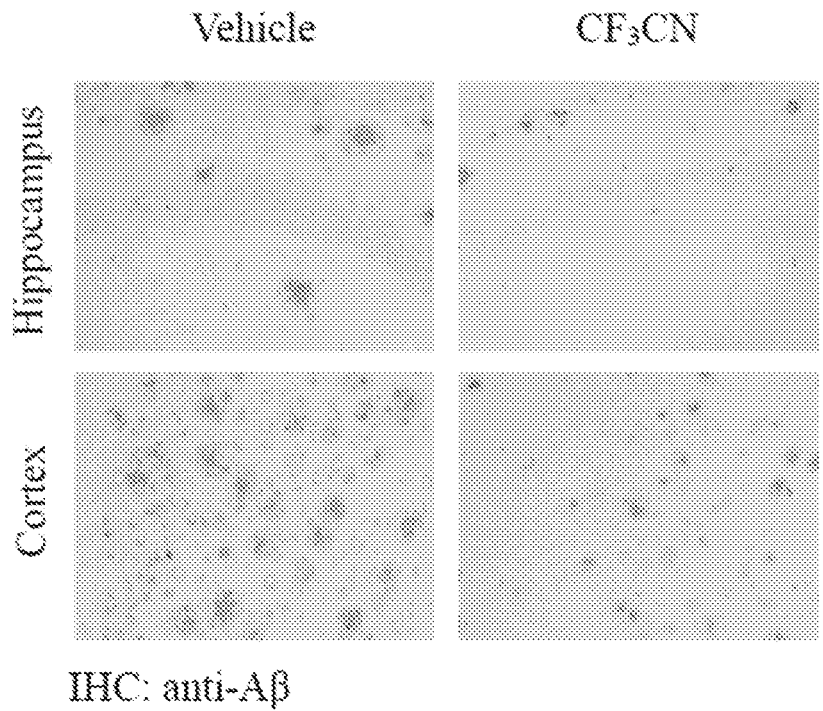
FIG. 3A shows data indicating CF3-CN decreases Aβ plaque deposition in 5×FAD mice. Immunohistochemistry of Aβ deposits in 5×FAD mice

The deposition of Aβ was tested by immunohistochemistry with anti-AP antibody. The Aβ deposition in both brain regions was significantly lower in CF3-CN-treated group than vehicle group (FIG. 3A). The effects of CF3-CN treatment on senile plaque formation were detected through immunofluorescence co-staining the brain section with anti-AP antibody and thioflavin-S. 5×FAD mice show evident plaque deposition both in the cortex and hippocampus at 6 months old. Strikingly, the number of plaques and plaque area fraction in both areas were significantly decreased in CF3-CN-treated mice as compared with vehicle control (FIG. 3B). To verify whether CF3-CN inhibits the production of Aβ, the concentrations of total Aβ42 and Aβ40 were quantitatively determined by ELISA. Aβ42 concentrations displayed a reduction trend by CF3-CN treatment; however, the differences were not statistically significant. Hence, these results suggest that chronic oral CF3-CN may prevent Aβ deposition other than production.

The hippocampus-dependent spatial memory of 5×FAD mice was tested by Morris water maze test. The average latency and swim path length for each of the 5 acquisition days were calculated and plotted. A two-way mixed analysis of variance (ANOVA) (Group X Training Day) on latency revealed a main effect of training day (p<0.01) and group (p<0.01) but not interaction. The area under curve (AUC) of latency in vehicle-treated 5×FAD mice was increased compared to non-transgenic control mice, indicating impaired acquisition of the spatial learning task. However, the learning impairment of 5×FAD mice was attenuated by CF3-CN treatment (FIG. 3C). A mixed two-way ANOVA on swim path distance also revealed a significant main effect of training day (p<0.01) and group (p<0.01) but not interaction. The AUC of the swim path distance in 5×FAD mice showed reduction trend by CF3-CN treatment with no significant statistic differences. The memory recall for the platform location was assessed in the probe trail when the platform was removed, and the mice were allowed to search for 60 s. When compared to non-transgenic control mice, vehicle-treated 5×FAD mice spent a significantly lower percentage of their time in the quadrant that formerly contained the hidden platform (FIG. 3D), indicating severe deficits in spatial memory recall. The 5×FAD mice treated with CF3-CN spent a significantly higher percentage of time in the target quadrant, demonstrating rescue of spatial memory. All groups of mice displayed comparable swim speeds.

Figure 4:
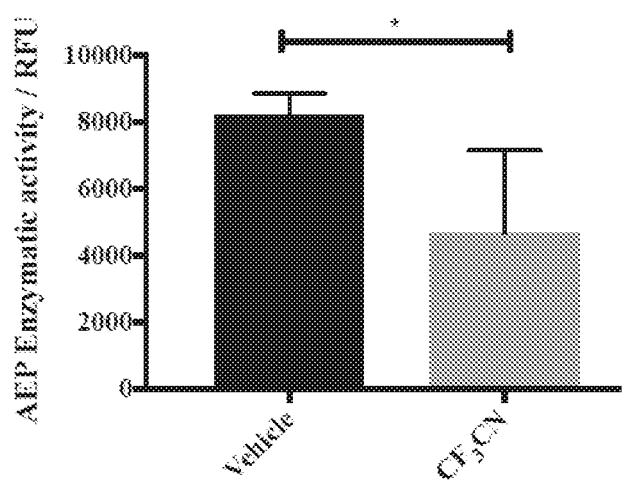
FIG. 4 shows data indicating CF3-CN inhibits AEP activation. The processing of APP and Tau by AEP was evaluated by western blot. CF3-CN significantly inhibited AEP activation by the reduction of AEP cleavage formation, which attenuated Tau and APP cleavage.

CF3-CN Inhibits AEP Activation and APP and Tau Proteolytic Cleavage in 5×FAD Mice Delta-secretase (AEP, asparagine endopeptidase) cleaves both APP and Tau, mediating AD pathogenesis. To explore whether CF3-CN affects the effect of AEP in AD pathologies, immunoblotting was conducted. Mature and active AEP was decreased by CF3-CN, correlating with reduction of AEP-cleaved APP N373, N585 and Tau N368 truncates in 5×FAD mouse brains (FIG. 4). To further investigate APP proteolytic cleavage activity by AEP, immunofluorescent co-staining was conducted on 5×FAD brain section with anti-APP C585 and AEP antibodies. APP C585 immunosignals were strongly inhibited by CF3-CN, coupled with AEP reduction. Furthermore, Tau N368 staining was also repressed by CF3-CN. Fitting with these observations, immunofluorescence revealed that AEP expression in Hippocampus was progressively attenuated by CF3-CN treatment. Enzymatic assay showed that AEP activity was blocked by CF3-CN at 3 mg/kg. In alignment with these observations, the inflammatory factors IL-6 in 5×FAD mouse brains was repressed by CF3-CN.

The invention claimed is:

1. A compound 4-(6-oxo-2-(trifluoromethyl)-3,6-dihydrochromeno[7,8-d]imidazol-8-yl)benzonitrile or salts thereof.

2. A pharmaceutical composition comprising a compound of claim 1 and a pharmaceutically acceptable excipient.

3. The composition of claim 2, wherein the pharmaceutical composition is in the form of a tablet, capsule, or pill.

4. The composition of claim 2, wherein the pharmaceutical composition is in sterilized and pH buffered aqueous solution.

5. A method of preventing or treating a BDNF and TrkB related disease or condition comprising the administering an effective amount of a pharmaceutical composition of claim 2, to a subject in need thereof.

6. The method of claim 5, wherein the disease or condition is depression, schizophrenia, obsessive-compulsive disorder, anorexia nervosa, bulimia nervosa, anxiety, amyotrophic later sclerosis, Alzheimer's disease, Huntington's disease, Rett syndrome, epilepsy, Parkinson's disease, dementia, diabetic neuropathy, peripheral neuropathy, obesity, or stroke.

7. The method of claim 5, wherein the method is improving memory in a subject diagnosed with dementia or related condition.

8. A compound 4-(1-methyl-2,6-dioxo-1,2,3,6-tetrahydrochromeno[7,8-d]imidazol-8-yl)benzonitrile or salt thereof.

9. A pharmaceutical composition comprising a compound of claim 8 and a pharmaceutically acceptable excipient.

10. The composition of claim 9, wherein the pharmaceutical composition is in the form of a tablet, capsule, or pill.

11. The composition of claim 9, wherein the pharmaceutical composition is in sterilized and pH buffered aqueous solution.

12. A method of preventing or treating a BDNF and TrkB related disease or condition comprising the administering an effective amount of a pharmaceutical composition of claim 9, to a subject in need thereof.

13. The method of claim 12, wherein the disease or condition is depression, schizophrenia, obsessive-compulsive disorder, anorexia nervosa, bulimia nervosa, anxiety, amyotrophic later sclerosis, Alzheimer's disease, Huntington's disease, Rett syndrome, epilepsy, Parkinson's disease, dementia, diabetic neuropathy, peripheral neuropathy, obesity, or stroke.

14. The method of claim 12, wherein the method is improving memory in a subject diagnosed with dementia or related condition.

\* \* \* \* \*